US007946848B2

(12) United States Patent
Discko, Jr.

(10) Patent No.: US 7,946,848 B2
(45) Date of Patent: May 24, 2011

(54) DISPENSER FOR LOW VISCOSITY DENTAL MATERIAL

(75) Inventor: John J. Discko, Jr., Trumbull, CT (US)

(73) Assignee: Centrix, Inc., Shelton, CT (US)

( * ) Notice: Subject to any disclaimer, the term of this patent is extended or adjusted under 35 U.S.C. 154(b) by 513 days.

(21) Appl. No.: 11/244,249

(22) Filed: Oct. 5, 2005

(65) Prior Publication Data
US 2006/0029905 A1    Feb. 9, 2006

Related U.S. Application Data

(63) Continuation of application No. 10/667,846, filed on Sep. 22, 2003, now Pat. No. 6,971,879.

(51) Int. Cl.
*A61C 3/00* (2006.01)
*B08B 1/00* (2006.01)

(52) U.S. Cl. .................. 433/163; 15/104.92

(58) Field of Classification Search ............ 433/77, 433/79, 163, 167; 206/366, 368, 207, 210; 132/74.5, 76.4; 15/104.92, 167.3
See application file for complete search history.

(56) References Cited

U.S. PATENT DOCUMENTS

| 4,232,784 | A | 11/1980 | Hesselgren | 206/210 |
|---|---|---|---|---|
| 4,440,181 | A | 4/1984 | Scherer | 132/73.5 |
| 4,530,726 | A | 7/1985 | Montiel | 134/6 |
| 4,671,306 | A | 6/1987 | Spector | 132/73 |
| 4,936,449 | A | 6/1990 | Conard et al. | 206/366 |
| 5,207,656 | A * | 5/1993 | Kranys | 604/256 |
| 5,293,960 | A * | 3/1994 | Majerowicz et al. | 184/13.1 |
| 5,339,477 | A * | 8/1994 | Warner et al. | 15/97.1 |
| 5,363,957 | A * | 11/1994 | Reichner | 206/349 |
| 5,525,059 | A * | 6/1996 | Lee | 433/141 |
| 5,967,778 | A | 10/1999 | Riitano | 433/77 |
| 6,036,490 | A | 3/2000 | Johnsen et al. | 433/102 |
| 6,053,184 | A * | 4/2000 | DeVone | 132/317 |
| 6,261,094 | B1 * | 7/2001 | Dragan | 433/90 |
| 6,325,565 | B1 * | 12/2001 | Girardot et al. | 401/266 |
| 6,419,114 | B1 | 7/2002 | Lenz et al. | 221/47 |
| 2002/0016619 | A1 * | 2/2002 | Iwahashi et al. | 607/88 |
| 2003/0168075 | A1 | 9/2003 | Schwartz | 132/309 |
| 2003/0186188 | A1 | 10/2003 | Tinnin | 433/77 |

* cited by examiner

*Primary Examiner* — Cris L Rodriguez
*Assistant Examiner* — Heidi M Eide
(74) *Attorney, Agent, or Firm* — Fattibene and Fattibene, LL; Paul A. Fattibene

(57) ABSTRACT

A dispenser made of a pliable material having a slit therein for dispensing primarily low viscosity materials. A block made of pliable foam contains a low viscosity material within a slit. Dental instruments or dental material applicators having an applicating end are inserted into the slit of the block, coating the applicator end with the low viscosity material. The resilient nature of the block material also helps to keep the dental instrument clean by wiping the instrument against the interior sides of the pocket formed by the slit. The present invention is particularly well suited for dispensing a lubricating material, such as a resin, on dental instruments used in working, shaping, or contouring a relatively viscous composite restorative material on a patient's tooth.

12 Claims, 3 Drawing Sheets

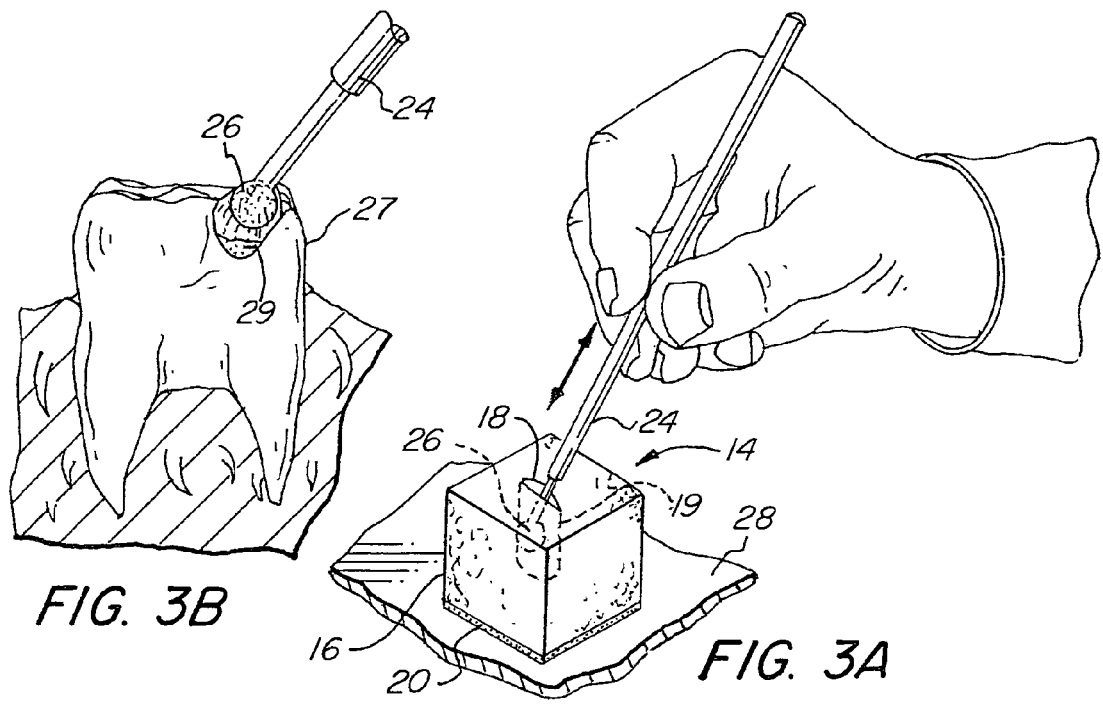
FIG. 3B
FIG. 3A
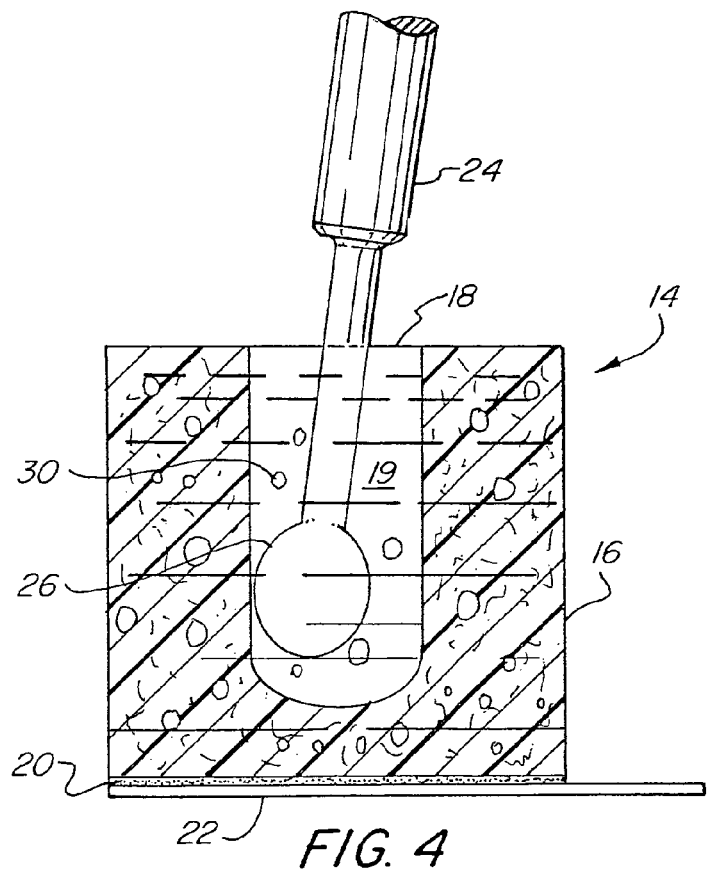
FIG. 4

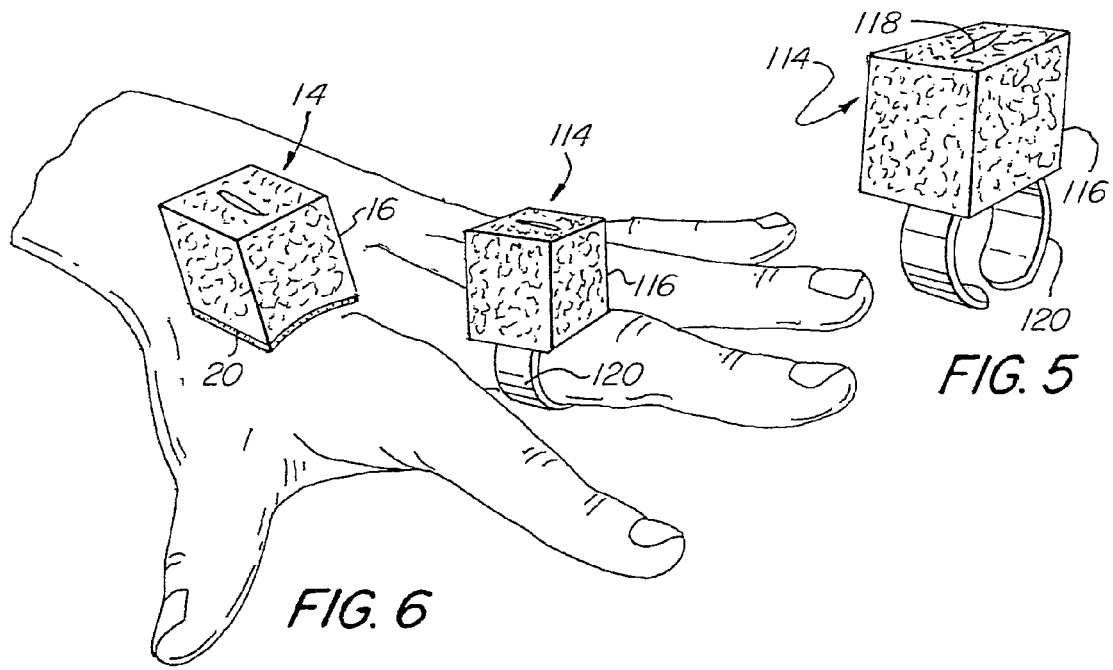
FIG. 6
FIG. 5
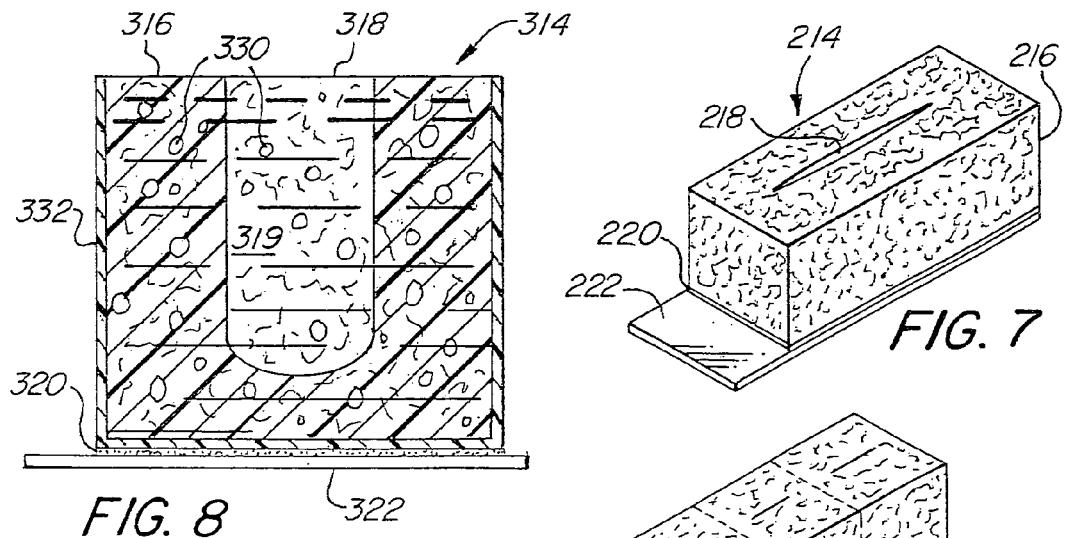
FIG. 8
FIG. 7
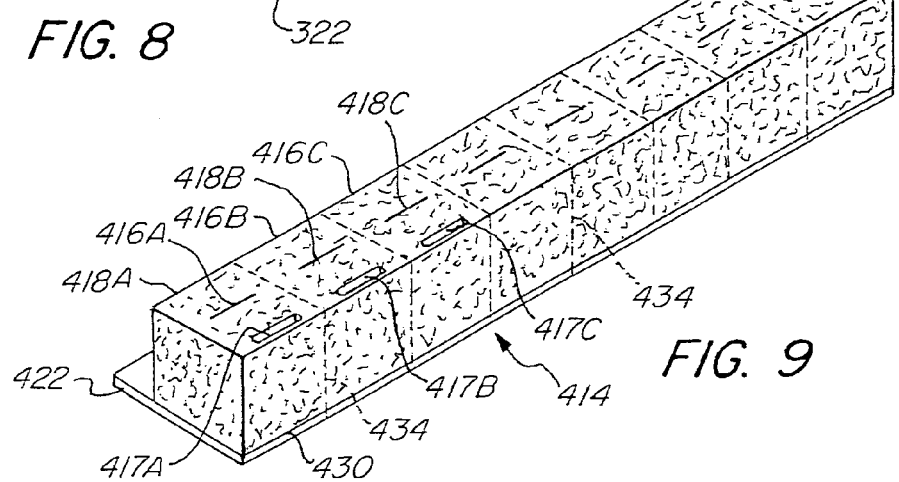
FIG. 9

DISPENSER FOR LOW VISCOSITY DENTAL MATERIAL

RELATED APPLICATIONS

This application is a continuation application of application Ser. No. 10/667,846, filed Sep. 22, 2003 now U.S. Pat. No. 6,971,879, which is herein incorporated by reference.

FIELD OF THE INVENTION

The present invention relates in general to a dispenser and application aid for applying dental materials, and more particularly to a dispenser capable of holding a single dose of low viscosity dental material for use with a dental instrument or applicator.

BACKGROUND OF THE INVENTION

There are many different kinds of dental materials that must be applied during different dental procedures. Some of these materials may be of relatively low viscosity and therefore difficult to apply or dispense in a single dose. Additionally, some dental procedures require the application sequentially of different types of materials. In some dental procedures, it may be necessary to coat the instrument with a lubricant, such as silicone, to prevent another dental material from sticking to the dental instrument. It is often difficult to work with a unit dose or small quantity of low viscosity dental material for this type of application in dental procedures.

A dental capsule for dispensing a low viscosity dental material is disclosed in U.S. Pat. No. 6,099,307 issuing to Discko on Aug. 8, 2000 entitled "Dental Capsule for Containing and Dispensing Low Viscosity Dental Material and Method of Filling and Applying Said Low Viscosity Material." Therein disclosed is a dental capsule used for storing and dispensing a low viscosity or liquid like dental material. A sponge is held within the body portion of the dental capsule which holds the dental material until a displaceable piston squeezes the sponge or foam material, causing the liquid dental material to be squeezed and dispensed from the dental capsule. Another low viscosity material dispensing system is disclosed in U.S. Pat. No. 6,328,715 issuing to Dragan et al on Dec. 11, 2001 and entitled "Unit Dose Low Viscosity Material Dispensing System." Therein disclosed is a sealed ampule having flexible walls adapted to be used in a delivery syringe for controllably dispensing a low viscosity material. The low viscosity dental material contained within the ampule is dispensed by advancing the plunger of a syringe, collapsing the ampule. While these low viscosity material delivery systems have been useful in applying a low viscosity material during a dental procedure, they often require a relatively large volume of low viscosity material and are not conveniently used in association with other conventional dental instruments or applicators. Additionally, it is often difficult to coat dental instruments with small quantities of a lubricant, which is often helpful in preventing restorative materials from sticking to the dental instrument during a dental procedure.

Composites and other restorative materials have been used in dentistry for a considerable time for restoring a tooth. Often, the composites are relatively viscous and sticky, and are picked up and placed with hand instruments for packing within a cavity in a tooth. While the packaging of these relatively viscous composite or restorative materials in capsules for dispensing with a syringe has minimized the need to use instruments, the use of instruments has not been eliminated. In many cosmetic dentistry applications, instruments are increasingly being used to shape and contour the composites or restorative materials once they have been placed on or in the tooth. However, many of these composite restorative materials are often sticky. This has often resulted in some of the composite restorative materials sticking to the instruments. The sticking results in pull back, which can generate voids and increase the amount of time needed to shape and contour or work the restoration. There is often a need to lubricate the instruments prior to working with the composite or restorative material with alcohol, resins, silicone or other lubricating agent. This has often been done by simply placing a quantity of liquid on a dish or a container in which the instrument is dipped. This is often wasteful and results in the possibility of cross-contamination and does not prevent the problem of excess material forming on a dental instrument.

Therefore, there is a need for a dispenser that can easily dispense small quantities of a low viscosity material and that can be used in combination with conventional dental instruments or applicator.

SUMMARY OF THE INVENTION

The present invention is a material dispenser for applying low viscosity dental materials and an application aid used with dental instruments. A block of pliable material, sufficiently absorbent to contain a quantity of low viscosity material, has a slit on one face. On another face or side of the block is means for attaching the block of material to a surface, such as a self-stick adhesive, or ring. A small quantity of low viscosity material to be used in a dental procedure is placed within the slit and held within the block of pliable dispensing material. A dental instrument or applicator is inserted into the slit so that the applicator or dental instrument is coated with the low viscosity material. By inserting and removing the dental instrument or applicator from the slit, excess material to be applied is prevented from accumulating, as well as other undesirable materials are cleaned or wiped off of the dental instrument or applicator. In another embodiment of the invention, the sides or faces of the block are coated with an impervious material.

Accordingly, it is an object of the present invention to provide a dispenser capable of dispensing low viscosity dental materials.

It is another object of the present invention to provide a dispenser containing a single dose of low viscosity material preventing waste of the low viscosity material and to aid in cleaning the dental instrument or applicator used during repeated applications of a material in a dental procedure.

It is an advantage of the present invention that light sensitive materials may be dispensed without prematurely activating the light sensitive material.

It is another advantage of the present invention that material spills are prevented.

It is yet another advantage of the present invention that multiple dispensers may be used in combination to dispense a plurality of different materials used in a dental procedure.

It is a further advantage of the present invention that it is inexpensive and disposable, preventing cross contamination.

It is a feature of the present invention that the dental material to be applied is contained in a pliable absorbent block of material.

It is another feature of the present invention that a slit in the absorbent material is used to aid in dosing and cleaning of a dental instrument or applicator.

It is a further feature of the present invention that an adhesive face aids in securing the dispenser to a surface.

BRIEF DESCRIPTION OF THE DRAWINGS

FIGS. 3A and 3B illustrate the application of the present invention in a dental procedure.

FIG. 4 is a cross section illustrating an embodiment of the present invention in greater detail.

FIG. 5 is a perspective view illustrating another embodiment of the present invention.

FIG. 6 is a perspective view illustrating different embodiments of the present invention attached to a user.

FIG. 7 is a perspective view illustrating another embodiment of the present invention.

FIG. 8 is a cross sectional view illustrating another embodiment of the present invention having an impervious outer membrane.

FIG. 9 is a perspective view illustrating another embodiment of the present invention utilizing a plurality of separable blocks or dispensers.

DETAILED DESCRIPTION OF THE PREFERRED EMBODIMENTS

Figure 1:
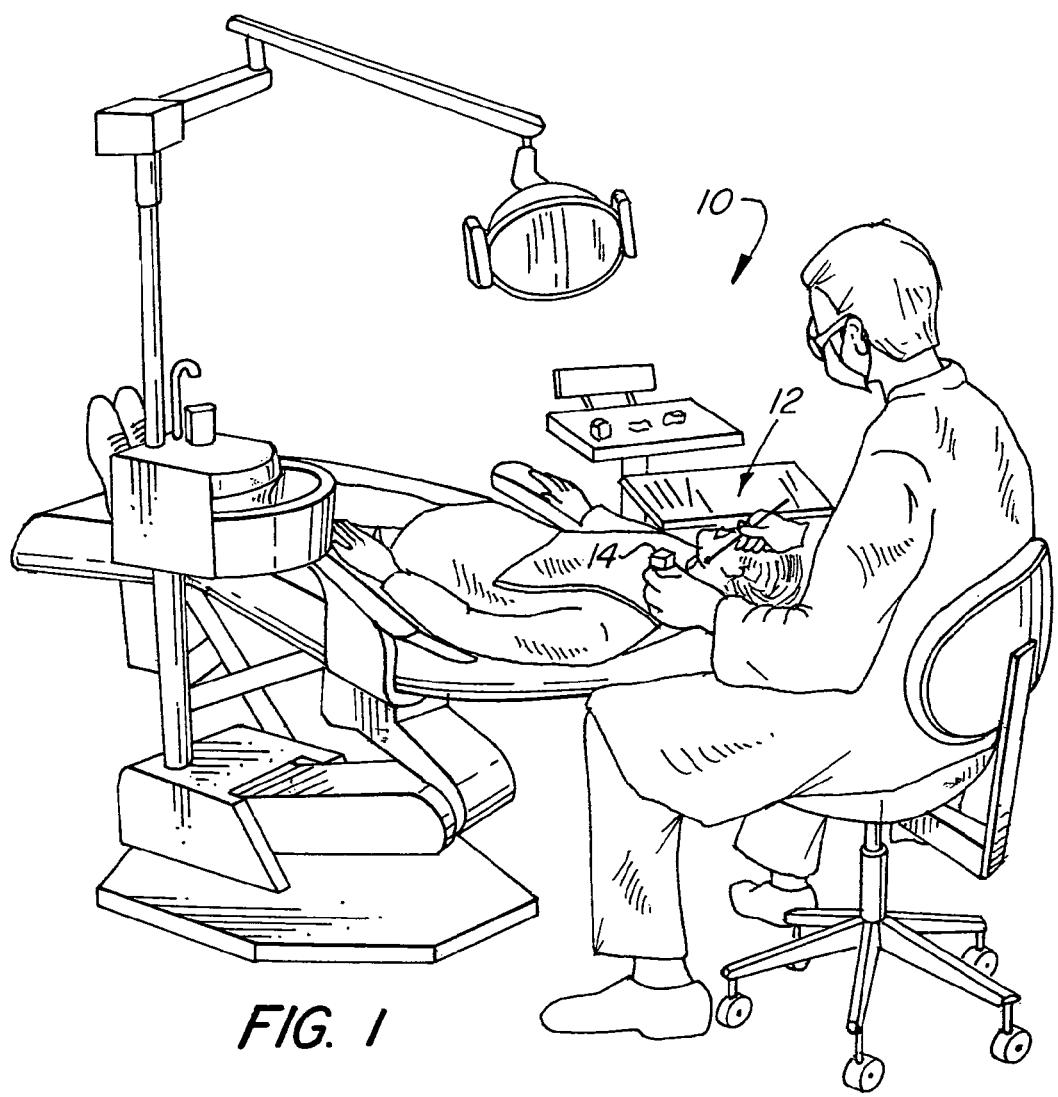
FIG. 1 schematically illustrates the application of the present invention in a dental operatory.

FIG. 1 illustrates the application of the present invention in a dental procedure. FIG. 1 illustrates a dental operatory 10 wherein dental instruments 12 are used on a patient. The dispenser 14 of the present invention is held by the doctor and used in combination with the dental instruments 12 in performing a dental procedure on a patient. The dispenser 14 is used to dispense low viscosity dental materials or aids in applying dental materials.

Figure 2:
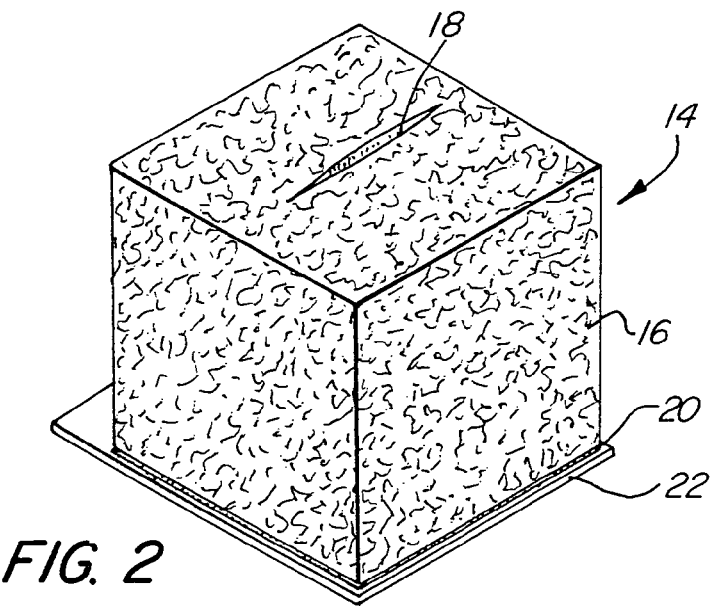
FIG. 2 is a perspective view illustrating an embodiment of the present invention.

FIG. 2 is a perspective view more clearly illustrating the dispenser 14 illustrated in FIG. 1. The dispenser 14 comprises a cube or block of foam material 16. The block 16 may be made of any resilient or pliable material such as foam. Preferably, the block 16 is made of a high density closed cell polyethylene foam. The block 16 should be impervious and non-interactive to most chemicals or dental materials for which it is intended to be used. Additionally, the block 16 may be made opaque so that it can contain light activated materials. The block 16 may be made of any convenient shape, such as a cube, rectangle, circle, or other similar or equivalent shape. On one face of the block 16 is an opening or a slit 18. The opening or slit 18 extends into the body of the block 16 and is adapted so as to permit a dental instrument or applicator to be placed therein. On another face of the block 16 is contact adhesive 20. Placed on the contact adhesive 20 is a protective backing 22. The block 16 is made of a material, which is resilient such that the opening or slit 18 is normally closed or nearly closed so as to partially seal in any material contained within the block 16. The material of the block 16 is sufficiently resilient to permit a dental instrument or applicator to be inserted through the opening or slit 18, yet permit the sides of the slit 18 to conform closely to the dental instrument or applicator. The words dental instrument and applicator are used interchangeably to define any device used to apply or work a material for use in a dental procedure.

Many different materials for application may be utilized with the dispenser 14 illustrated in FIG. 2. For example, the dispenser 14 may be pre-dosed with a material, or a doctor may add any desired material into the slit 18 for use in a dental procedure. A lubricant such as a light activated resin may be placed within the dispenser 14. Other lubricants such as silicone, Teflon, glycerin, or other lubricants may be used. The lubricants help to clean, condition, and lubricate the dental instruments. This is particularly advantageous in that some dental materials, such as restorative materials, may stick to dental instruments unless the dental instruments are pre-lubricated. If the dental instruments stick to the restorative materials, the dentist cannot properly shape the restoration. Additionally, other relatively low viscosity materials may be used in a dispenser 14 such as pit and fissure sealant, slightly filled resins, bonding agents, caries detector dye, hemostatic agents, disinfectant agents, bleaches, stains, tints, chemical activating agents, or other similar relatively low viscosity materials desired to be applied or used in a dental procedure. FIGS. 3A and 3B illustrate the use of the present invention in applying a dental material used in a dental procedure. Opening or slit 18 formed in the block 16 forms a pocket 19. The applicator end 26 of a dental material applicator or instrument 24 may be placed within the pocket 19. The opening or slit 18 is normally closed due to the resiliency of the material of the block 16 until the applicator end 26 of a dental material applicator 24 is pushed through the slit 18. Preferably, the slit 18 has a longitudinal dimension at least three times the diameter or lateral dimension of the applicator end 26 of a dental material applicator. A dental material is held within the pocket 19 and the material of the block 16. The block 16 may be held in position securely by pressure sensitive adhesive 20 attaching to a surface 28. The use of the pressure sensitive adhesive 20 or other means for securing the block 16 permits the dentist to use both hands in a dental procedure, without having to use one hand to hold the block 16. After insertion of the instrument or dental material applicator 24 into the dispenser 14, the instrument or dental material applicator 24 may be used in a dental procedure as illustrated in FIG. 3B. In FIG. 3B, the instrument or dental material applicator 24 is used to prepare a cavity 29 formed in a tooth 27.

In a preferred application, the dental material contained within the dispenser 14 is a lubricant or bonding agent such as a light activated resin, which is compatible with a restorative or composite material for filling a cavity or other application. The lubricant or resin contained within the dispenser 14 is used to lubricate the applicator end 26 so that the applicator end 26 does not stick to the composite or restorative material used to restore or cosmetically improve the appearance of the tooth 27. The applicator can also impart a glaze, bond, or sealing agent to improve the surface finish of the final restoration. The applicator 24 also functions to clean any excess composite or restorative material that may form on the applicator end 26 of the instrument or dental material applicator 24 during the dental procedure. Therefore, a relatively clean instrument or dental material applicator 24 is utilized in shaping or finishing the restoration of the tooth 27.

FIG. 4 is a cross section of the dispenser 14, more clearly illustrating its structure. Within the block 16, slit 18 forms a pocket 19. Within the pocket 19, a dental material 30 is placed. The applicator end 26 of an instrument or dental material applicator 24 is placed through slit 18 into the pocket 19. The dental material 30 coats the applicator end 26. The resilient sidewalls of the block 16 also act to wipe any excess dental material 30 from the applicator end 26, as well as to wipe off any other material that may accumulate on the applicator end 26 during a dental procedure. One face of the block 16 has a contact adhesive 20 formed thereon, initially protected by a protective backing 22. The contact adhesive 20 is used to attach the block 16 to any convenient surface so that the doctor does not have to use a hand to hold onto the block 16 during use.

FIG. 5 illustrates another embodiment of the invention utilizing means for securing the dispenser during use. Dispenser 114 comprises a block 116 having a slit 118 therein. On one face of the block 116 is placed a ring 120. The ring 120 is of a size adapted to fit over the finger of a dentist or assistant.

FIG. 6 illustrates the application of the present invention and the attachment onto a user or dentist's hand. In one embodiment, the dispenser 14 may be attached to a user's hand by the contact adhesive 20 on one face of the cube 16. In another embodiment of the invention, the dispenser 114 may be held on a finger with ring 120 attached to block 116. Any other known or equivalent means for attaching may be utilized in securing the dispenser of the present invention onto a surface or the user's hand or other body part.

FIG. 7 illustrates another embodiment of the present invention. The dispenser 214 comprises an elongated block 216 having an elongated opening or slit 118 therein. On one face of the elongated block 216 is contact adhesive 220. The contact adhesive 220 is initially protected by a protective backing 222. The elongated block 216 may be a rectangle, or other suitable shape. This permits the opening or slit 218 to be larger, creating additional surface area and permitting the dispenser 214 to hold more material, as well as to accommodate different sizes or shapes of instruments or dental material applicators. It should be appreciated that the block used in forming the present invention may be made of a variety of dimensions, shapes, and sizes and in no way should be limited to the cube shape or rectangular shape illustrated in the preferred embodiments.

FIG. 8 illustrates another embodiment of the present invention utilizing an exterior impervious membrane. The dispenser 314 comprises a block 316 made of a foam material having a slit 318 therein, forming a pocket 319. A dental material 330 is contained within the pocket 319. The material 330 is also impregnated or contained within the block 316. An impervious material 332 is formed on the faces or sides of the block 316, retaining the dental material 330 within the block 316. A contact adhesive 320 is placed on one face of the impervious material 332. A protective backing 322 initially protects the contact adhesive 320. In this embodiment, a more porous material may be utilized in block 316 for holding additional dental material 330. The impervious material 332 prevents the dental material 330 contained within the block 316 from soaking through the sides of the block 316. The impervious material 332 may be any impervious material, such as plastic, rubber, or any other equivalent material impervious to the dental material 330 contained within the block 316. Additionally, the impervious material 332 may be made of a material that blocks the actinic radiation that may activate a light sensitive material contained within the block 316.

FIG. 9 illustrates another embodiment of the present invention using a plurality of dispensers. The plurality of dispensers 414 may be formed in a strip that is easily separated along separation lines 434. The separation lines 434 may be weakened portions or a partial cut formed between adjacent dispensers. Each of the plurality of dispensers comprises a block, with only the first three identified as blocks 416A, 416B, and 416C. All of the blocks have slits therein, with the first three identified as slits 418A, 418B, and 418C. A contact adhesive 430 may be applied to one face of the plurality of blocks having a protective backing 422 formed thereon. The embodiment illustrated in FIG. 9, having a plurality of dispensers 414, may be utilized as a packaging and dispensing convenience, but also may be utilized to provide convenient dispensing of multi-part components of a dental material used in a dental procedure. For example, block 416A may contain a first dental material and block 416B may contain a second dental material that may be required to be applied subsequent to the first dental material contained in block 416A. The use of a plurality of different dispensers 414 therefore makes possible the separation of small quantities of dental material that, when combined, may react during a dental procedure. Such component part chemically activated materials could be used in a wide variety of dental procedures, such as in bonding, etching, desensitizing, or other like materials. A self etching bonding agent or the like could also be used. The blocks 416A, 416B, and 416C may be made visually distinct so as to make them uniquely identifiable. This could be done with labels 417A, 417B, and 417C placed on each respective block 416A, 416B, and 416C or each block being a different color. Therefore, each component of a multi-component material system is easily identified.

The present invention provides a relatively inexpensive and economical means for dispensing small quantities of a relatively low viscosity material. The present invention can readily be provided in a pre-dosed form or without any material to be applied so that the doctor can add any material of choice. The compliant nature of the block of material, in combination with the slit formed therein, has the advantage that the slit is closed until an instrument or dental material applicator is inserted therein. This makes the use of a light sensitive material practical. The slit being closed protects the light sensitive material from reacting due to ambient light. Light activated materials are generally difficult to dispense because of the difficulty of maintaining them in a light tight container while permitting easy access for use. While the present invention is ideally suited for lubricating dental instruments, it may also be used to apply other, more viscous and sticky dental compositions. Different materials having full range of viscosities may be used with the present invention. Additionally, many different other materials may be easily dispensed.

While different preferred embodiments have been illustrated and described, it will be obvious to those skilled in the art that various modifications may be made without departing from the spirit and scope of this invention.

What is claimed is:

1. A dental material dispenser for use with a dental instrument used in a tooth restoration procedure comprising:
   a dental instrument having an applicator end;
   a pliable closed cell foam integral block of material;
   a single slit opening normally closed and forming a pocket having a bottom formed in said pliable closed cell foam material adapted to receive the applicator end of said dental instrument a longitudinal dimension of said single slit opening being at least three times a dimension of the applicator end of said dental instrument, whereby the applicator end of said dental instrument may be pushed through the longitudinal dimension of said single slit opening;
   a resin placed within said single slit opening, said resin compatible with an initially viscous and sticky composite or restorative material used in the tooth restoration procedure,
   whereby the dental material dispenser is capable of holding said resin to be dispensed and the applicator end is cleaned and lubricated with said resin by the applicator end being pushed through the longitudinal dimension of said single slit opening.

2. A material dispenser as in claim 1 wherein:
said pliable closed cell foam material comprises polyethylene.

3. A material dispenser as in claim 1 wherein:
the block has six substantially planar sides.

4. A material dispenser as in claim 1 further comprising:
an impervious material placed around said pliable closed cell foam material.

5. A material dispenser as in claim 1 further comprising:
means for holding said pliable closed cell foam in position.

6. A material dispenser as in claim 5 wherein:
said means for holding comprises a pressure sensitive adhesive placed on an entire side surface of the integral block of material opposing a side having said single slit opening.

7. A material dispenser as in claim 5 wherein:
said means for holding comprises a ring.

8. A dental material dispensing system used in restoring a tooth in a dental procedure comprising:
a dental instrument having an applicator end for shaping or finishing an initially viscous and sticky restorative or composite material used in restoring a tooth;
a block of pliable material;
a single slit only, said single slit being normally closed and forming a pocket having a closed bottom formed in one side of said block of pliable material, said single slit and the pocket having a shape to receive the applicator end of said dental instrument, said single slit only having a longitudinal dimension being at least three times a dimension of the applicator end of said dental instrument, whereby the applicator end of said dental instrument is pushed through the longitudinal dimension of said single slit only;
a pressure sensitive adhesive placed on a side of said block of pliable material opposite said single slit, whereby said block of pliable material may be held in a desired position; and
a dental resin placed in said opening and held by said block of pliable material, wherein said dental resin is compatible with the initially viscous and sticky restorative or composite material,
whereby the applicator end of said dental instrument is capable of being inserted into said single slit and pushed through the longitudinal dimension of said single slit only thereby cleaning the applicator end and coated the applicator end with said dental resin for preventing the initially viscous and sticky restorative or composite material from sticking to the applicator end of said dental instrument during the dental procedure.

9. A dental material dispensing system used in a dental procedure as in claim 8 wherein:
said block of pliable material comprises closed cell foam.

10. A dental material dispensing system used in a dental procedure as in claim 8 wherein:
said block of pliable material comprises a cube having six sides.

11. A unit dose low viscosity dental resin dispensing and dental instrument cleaning system used in restoring a tooth in a dental procedure to restore a tooth comprising:
an initially viscous and sticky restorative or composite material;
a dental instrument having an applicating end adapted to shape the initially viscous and sticky restorative or composite material used to restore a tooth, the applicating end having a lateral dimension;
a block of pliable material;
a single slit normally closed and forming a pocket with a closed bottom formed in one side of said block of pliable material, said single slit having a longitudinal dimension, the longitudinal dimension being at least three times the lateral dimension of the applicating end of said dental instrument, whereby the applicating end of said dental instrument is pushed through the longitudinal dimension of said single slit; and
a dental resin placed within said block of pliable material, said dental resin is compatible with said initially viscous and sticky restorative or composite material and when placed on the applicating end of said dental instrument prevents said initially viscous and sticky restorative or composite material from sticking to the applicating end when working said initially viscous and sticky restorative or composite material in the dental procedure to restore the tooth,
whereby the applicating end of said dental instrument is capable of being inserted into said single slit and pushed through the longitudinal dimension of said single slit thereby cleaning the applicating end and coated the applicating end with said dental resin so that said initially viscous and sticky restorative or composite material is easily applied and worked creating an improved restoration.

12. A unit dose low viscosity lubricant and dental instrument cleaning system used in a dental procedure as in claim 11 further comprising:
a pressure sensitive adhesive placed on a side of said block of pliable material.

* * * * *